United States Patent
Seo et al.

(10) Patent No.: US 11,946,031 B2
(45) Date of Patent: Apr. 2, 2024

(54) YARN FOR CELL CULTURE SCAFFOLD AND FABRIC COMPRISING THE SAME

(71) Applicant: AMOGREENTECH CO., LTD., Gimpo-Si (KR)

(72) Inventors: In Yong Seo, Seoul (KR); Seon Ho Jang, Seoul (KR); Chan Kim, Gwangju (KR); Seoung Hoon Lee, Paju-si (KR); Song Hee Koo, Gimpo-si (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 572 days.

(21) Appl. No.: 16/309,649

(22) PCT Filed: Jun. 13, 2017

(86) PCT No.: PCT/KR2017/006142
§ 371 (c)(1),
(2) Date: Dec. 13, 2018

(87) PCT Pub. No.: WO2017/217736
PCT Pub. Date: Dec. 21, 2017

(65) Prior Publication Data
US 2019/0338233 A1    Nov. 7, 2019

(30) Foreign Application Priority Data
Jun. 13, 2016    (KR) ......................... 10-2016-0073293

(51) Int. Cl.
*C12M 1/12*    (2006.01)
*A61L 27/16*    (2006.01)
(Continued)

(52) U.S. Cl.
CPC ............. *C12M 25/14* (2013.01); *A61L 27/16* (2013.01); *A61L 27/38* (2013.01); *A61L 27/54* (2013.01);
(Continued)

(58) Field of Classification Search
CPC ......... C12M 25/14; C12M 21/08; D02G 3/02; D02G 3/045; D02G 3/38; D02G 3/448;
(Continued)

(56) References Cited

U.S. PATENT DOCUMENTS

2015/0283543 A1* 10/2015 McKean ................ C12M 25/14
435/396
2018/0251714 A1*  9/2018 Liu ......................... C12M 41/46

FOREIGN PATENT DOCUMENTS

JP       2005226210 A      8/2005
KR       100875189 B1     12/2008
(Continued)

OTHER PUBLICATIONS

Machine Translation of KR101075882 (Year: 2011).*
(Continued)

*Primary Examiner* — Jenna N Chandhok
(74) *Attorney, Agent, or Firm* — ROTHWELL, FIGG, ERNST & MANBECK, P.C.

(57) ABSTRACT

Provided is yarn for a cell culture scaffold. The yarn for a cell culture scaffold according to an exemplary embodiment of the present invention includes slitting yarn produced by cutting a compressed nanofiber web to a predetermined width. Accordingly, by creating microenvironments suitable for migration, proliferation and differentiation of cells, cell viability may be enhanced and cells may be three-dimensionally proliferated. In addition, a scaffold according to the present invention has a mechanical strength sufficient for prevention of disruption of the scaffold which occurs during (Continued)

cell culture, such that cells may be stably proliferated. Further, the scaffold according to the present invention uses slitting yarn formed of the compressed nanofiber web, thereby having pores with various sizes, and therefore cell proliferation and cell viability may be enhanced by creation of an extracellular matrix-like environment.

9 Claims, 6 Drawing Sheets

Specification includes a Sequence Listing.

(51) Int. Cl.
- *A61L 27/38* (2006.01)
- *A61L 27/54* (2006.01)
- *C12N 5/00* (2006.01)
- *D02G 3/02* (2006.01)
- *D02G 3/04* (2006.01)
- *D02G 3/38* (2006.01)
- *D02G 3/44* (2006.01)
- *D02J 3/02* (2006.01)

(52) U.S. Cl.
CPC ............. *C12N 5/0068* (2013.01); *D02G 3/02* (2013.01); *D02G 3/045* (2013.01); *D02G 3/38* (2013.01); *D02G 3/448* (2013.01); *D02J 3/02* (2013.01); *C12N 2533/30* (2013.01); *D10B 2509/00* (2013.01)

(58) Field of Classification Search
CPC .... D02G 3/06; C12N 5/0068; C12N 2533/30; D02J 3/02; A61L 2400/12
See application file for complete search history.

(56) References Cited

FOREIGN PATENT DOCUMENTS

| | | |
|---|---|---|
| KR | 20080104932 A | 12/2008 |
| KR | 101075882 B1 | 10/2011 |
| KR | 20120097948 A | 9/2012 |

OTHER PUBLICATIONS

Machine Translation of KR2008104932 (Year: 2008).*
Machine Translation of JP2005226210 (Year: 2005).*
Krishnan, Ranganathan et al. "Green Processing of Nanofibers for Regenerative Medicine." Macromol. Mater. Eng. 2013. 298: 1034-1058. (Year: 2013).*
Bružauskaitė, I., Bironaitė, D., Bagdonas, E. et al. Scaffolds and cells for tissue regeneration: different scaffold pore sizes—different cell effects. Cytotechnology 68, 355-369 (2016). Published Online Jun. 20, 2015 (Year: 2016).*
International Search Report cited in PCT/KR2017/006142, dated Oct. 16, 2017, 2 pages.

* cited by examiner

YARN FOR CELL CULTURE SCAFFOLD AND FABRIC COMPRISING THE SAME

CROSS REFERENCE TO RELATED APPLICATION

This application is a 35 U.S.C. 371 National Phase Entry Application from PCT/KR2017/006142, filed Jun. 13, 2017, which claims the benefit of Korean Patent Application No. 10-2016-0073293 filed on Jun. 13, 2016, the disclosures of which are incorporated herein in their entireties by reference.

SEQUENCE LISTING

The present application includes a Sequence Listing filed in electronic format. The Sequence Listing is entitled "4669-104_5 T25.txt" created on Dec. 10, 2018, and is 12,000 bytes in size. The information in the electronic format of the Sequence Listing is part of the present application and is incorporated herein by reference in its entirety.

TECHNICAL FIELD

The present invention relates to a cell culture scaffold, and more particularly, to yarn for a cell culture scaffold which has improved mechanical properties and is suitable for three-dimensional culture of cells, and a fabric having the same.

BACKGROUND ART

Recently, according to expansion of the use of cultured cells in disease treatment, interest in and research on cell culture are increasing. Cell culture is a technique for collecting cells from a living organism and culturing the cells outside the living organism, and the cultured cells may be used in treatment of various diseases through differentiation into various types of tissue of a body, for example, the skin, organs, nerves, etc. to be grafted into the body, or grafting in an undifferentiated state to attain engraftment and differentiation at the same time.

A field associated with such cell culture is tissue engineering, which is an interdisciplinary study that applies existing scientific fields such as cytology, life science, engineering, medicine, etc., and thus novel fusion technology for understanding a relationship between the structure and function of living tissue, replacing damaged tissue or a damaged organ with normal tissue and regenerating the damaged tissue or organ has been studied.

Such fusion technology is continuously receiving a great deal of attention in a conventional cell culture field or a tissue engineering field using the same, and one of tasks which are being studied and developed is a study of a material and structure of a scaffold which can culture/differentiate cells and be grafted into human tissue while including the cells. That is, to examine an influence of a specific material on the human body, a toxicity experiment for the specific material using cultured cells may be more suitable as an in vitro cytotoxicity test model that is similar to an actual human cell structure, compared with that performed using a cell cluster cultured/distributed in a three-dimensional structure, which is similar to the actual human cell structure. In addition, to graft cultured cells to human tissue, cells or tissue grafted when a cell cluster cultured/differentiated in a three-dimensional structure similar to the actual human tissue may play sufficient function and role.

However, in the case of scaffolds for cell culture or tissue engineering, which have developed so far, cells are not cultured in a structure similar to the human body and cell viability is not high, and therefore cells cultured using this are not suitable for use as an in vitro experiment model or cells for grafting. In addition, when a scaffold for cell culture or tissue engineering is produced of a nanofiber suitable for a cell size, it has a low mechanical property and thus is not suitable for cell culture.

In addition, when biodegradable compounds which are selected to avoid a separate operation for removing a scaffold after being grafted into a living organism are typically applied to the scaffold, due to a low mechanical property, the shape of the scaffold may be transformed or destroyed during cell culture.

Further, since typical biodegradable compounds are components easily decomposed by moisture, they are decomposed by a solvent included in a culture medium added during cell culture, and therefore the mechanical strength of a scaffold is more weakened.

For this reason, there is an urgent demand for development of a scaffold which can provide culture environments similar to the human body, ensure a proper space required for cell culture and a sufficient mechanical strength for each cell, be easily manufactured with a desired structure, and prevent detachment of cells from the scaffold during culture to increase cell viability and three-dimensionally grow the cells.

DISCLOSURE

Technical Problem

The present invention is devised by taking the above-mentioned problems into account, and thus directed to providing high-strength yarn for a cell culture scaffold to improve cell viability and three-dimensionally proliferate cells by creating microenvironments suitable for migration, proliferation and differentiation of cells.

In addition, the present invention is also directed to providing yarn for a cell culture scaffold which can stably proliferate cells by exhibiting a sufficient mechanical strength for preventing destruction of a scaffold during cell culture.

In addition, the present invention is also directed to providing yarn for a cell culture scaffold which can easily create microenvironments suitable for cell culture.

Further, the present invention is also directed to providing yarn for a cell culture scaffold which can culture cells to have a similar shape/structure as in an actual animal body such that the cells can be more suitable for being applied to an in vitro experimental model or grafting into an animal.

Moreover, the present invention is also directed to providing yarn and a fabric for a cell culture scaffold, which can be widely applied in various types of products used in a cell culture or tissue engineering field, including a bioreactor, a cell culture container, etc., using the yarn for a cell culture scaffold described above.

Technical Solution

To solve the above-described problems, the present invention provides yarn for a cell culture scaffold, which includes slitting yarn produced by cutting a compressed nanofiber web to a predetermined width.

According to an exemplary embodiment of the present invention, the yarn is formed by twisting multiple fiber strands including the slitting yarn.

In addition, the nanofiber web may include a nanofiber formed of any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly(alkylene oxide), a poly(amino acid), a poly(allylamine), polyphosphazene and a polyethyleneoxide-polypropyleneoxide block copolymer, or a nanofiber formed of any one or more biodegradable components selected from the group consisting of polycaprolactone, polydioxanone, polyglycolic acid, poly(L-lactide) (PLLA), poly(DL-lactide-co-glycolide) (PLGA), polylactic acid and polyvinyl alcohol.

In addition, the slitting yarn may have a ratio of a basis weight to a thickness of 1:0.8 to 1.7.

In addition, the slitting yarn may have a width of 0.1 to 8 mm.

In addition, the nanofiber web may be formed of scaffold fibers having an average diameter of 100 nm to 1 μm.

In addition, in a diameter distribution of the scaffold fibers, a diameter dispersion coefficient (E) of the scaffold fibers may be 8 to 25%.

In addition, an air permeability of the compressed nanofiber web may be 0.8 to 10 cfm.

In addition, the slitting yarn may have a basis weight of 7 to 30 g/m$^2$, and a thickness of 7 to 30 μm.

In addition, the nanofiber web may include a physiologically active component which promotes induction of any one or more of adhesion, migration, growth, proliferation and differentiation of cells.

In addition, the physiologically active component may include any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell.

In addition, the present invention provides a fabric for a cell culture scaffold which includes the yarn for a cell culture scaffold according to the present invention.

In addition, the present invention provides a cell incubator, which includes yarn for a cell culture scaffold according to the present invention; and a cell cluster cultured in outer and inner spaces of a nanofiber web of the yarn.

According to an exemplary embodiment of the present invention, the cell cluster may include any one or more types of stem cells selected from the group consisting of totipotent stem cells, pluripotent stem cells, multipotent stem cells, oligopotent stem cells and single stem cells, and/or one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

Amino acid sequences used in the present invention were written with abbreviations as shown in Table 1 below according to the IUPAC-IUB Nomenclature.

TABLE 1

| IUPAC-IUB name | Symbol | Simplified form |
|---|---|---|
| Alanine | A | Ala |
| Arginine | R | Arg |
| Asparagine | N | Asn |
| Cysteine | C | Cyn |
| Glutamic acid | E | Glu |
| Glutamine | Q | Gln |
| Glycine | G | Gly |
| Histidine | H | His |
| Isoleucine | I | Ile |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Advantageous Effects

According to the present invention, microenvironments are more easily created to be suitable for migration, proliferation and differentiation of cultured cells, such that a cell proliferation rate and cell viability can be improved. In addition, since mechanical strength and proper elongation can be ensured, cells can be cultured more stably.

Further, the cultured cells can be cultured to have a similar shape/structure as in an actual animal body such that the cells can be suitable for being applied to an in vitro experimental model or grafting into an animal.

In addition, the yarn according to an exemplary embodiment of the present invention can be modified with a material that helps cell culture/differentiation such that cell proliferation and cell viability can be further improved. Therefore, cells cultured using the yarn can be more easily implemented in a three-dimensional shape. For this reason, the yarn according to the present invention can be very suitable for use in cell culture and tissue engineering fields, and thus can be widely applied to various products in the corresponding fields.

DESCRIPTION OF DRAWINGS

FIGS. 7A-7C illustrate an intermediate step for producing slitting yarn included in an exemplary embodiment of the present invention, in which FIG. 7A is an image of the slitting yarn subjected to first slitting to a width of 50 mm, FIG. 7B is an image illustrating a process of precisely slitting the first-slit yarn to a width of 1.5 mm, and FIG. 7C is an image illustrating a process of winding the slitting yarn with a width of 1.5 mm, produced according to the process illustrated in FIG. 7B.

MODES OF THE INVENTION

Figure 1:
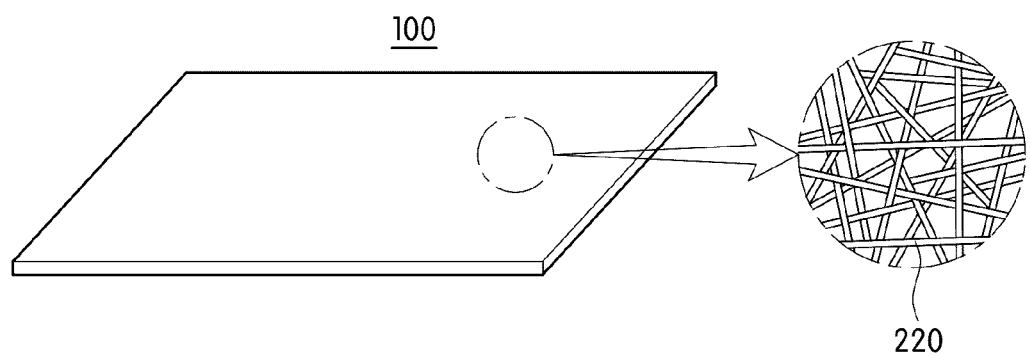
FIG. 1 shows a perspective view and a partial enlargement of a nanofiber web compressed before slitting yarn included in an exemplary embodiment of the present invention is produced.

Hereinafter, embodiments of the present invention will be described in detail with reference to the accompanying drawings so that those of ordinary skill in the art can easily carry out the present invention. The present invention may be implemented in a variety of different forms, and is not limited to the embodiments described herein. For clear explanation of the present invention in the drawings, parts that are not related to the description are omitted, and the same numerals denote the same or like components throughout the specification.

Figure 2:
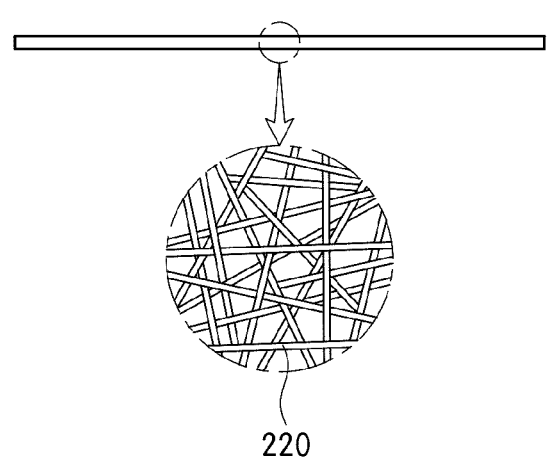
FIG. 2 shows a cross-sectional view and a partial enlargement of slitting yarn included in an exemplary embodiment of the present invention.

Referring to FIGS. 1 and 2, yarn for a cell culture scaffold according to an exemplary embodiment of the present invention includes slitting yarn 200 produced by cutting a nanofiber web 100 which includes a scaffold fiber 220 and is compressed to a predetermined width.

The nanofiber web 100 may have a three-dimensional network structure formed of at least one strand of the scaffold fiber 220.

Specifically, the three-dimensional network structure may be formed by arranging/stacking one strand of the scaffold fiber 220 folded several times without orientation. Alternatively, the nanofiber web 100 may include a plurality of scaffold fibers 220, and each scaffold fiber 220 may be independently folded and/or arranged/stacked without determination of a fiber length direction, thereby forming a three-dimensional network structure.

Here, adhesion or fusion may occur at different spots on one strand of the scaffold fiber 220 where contact occurs and/or at spots where different scaffold fibers 220 are in contact. Therefore, the three-dimensional network structure may be more complicated, cells loaded in a scaffold may be migrated/proliferated into pores formed in a three-dimensional network structure, and it can be advantageous for culturing cells using a cell cluster having a three-dimensional shape/structure.

In addition, to increase the proliferation rate and viability of cells cultured inside/outside the scaffold, supply of nutrients required for cell proliferation is important, the nanofiber web 100 having a three-dimensional network structure has a variety of very complicated fluid channels through which a culture medium containing nutrients can pass to easily provide nutrients to cells located in the scaffold, such that cell death can be prevented and cell proliferation can be improved.

However, the nanofiber web designed to have various fluid channels, when being compressed to implement slitting yarn, is decreased in the number of fluid channels and average pore size such that a culture medium does not pass through the channel at a desired level and cells cannot be migrated and proliferated into pores. In this case, it may be difficult to attain three-dimensional culture of cell clusters.

Accordingly, the slitting yarn 200 or the compressed nanofiber web 100 forming the same may have a basis weight of 3 to 50 $g/m^2$, preferably 7 to 30 $g/m^2$. If the basis weight is less than 3 $g/m^2$, there is a tendency that handleability is lowered and a slitting process is not easy and unstable, and productivity is probably lowered due to frequent yarn breakage. In addition, if the basis weight is more than 50 $g/m^2$, pores and fluid channels in the nanofiber web are considerably reduced due to great compression of the nanofiber web, and the cross-sectional shape of the scaffold fiber forming the nanofiber web may be changed into a pressed elliptical shape or the like. In this case, a morphological change in the surface or inner space of the nanofiber web is induced, thus, it is difficult to achieve three-dimensional culture and growth of cells. The relationship between the morphology of the nanofiber web and three-dimensional culture of the cells will be described later.

In addition, the slitting yarn 200 may have a thickness of 7 to 30 μm, preferably 9 to 25 μm. When the slitting yarn 200 has a thickness of less than 7 μm, handleability may be lowered, and due to a low mechanical strength, yarn breakage may occur in a twisting process performed independently or after braiding of several strands of the slitting yarns, such that it can be difficult to stably culture cells. In addition, when the thickness is lowered due to an excessive compression process, porosity and an average pore size may be reduced, and a surface morphology may become flat such that it can be difficult to stably culture cells. In addition, if the thickness is more than 30 μm, while being changed according to the basis weight, cells may be frequently detached during culture due to an unstable surface morphology when the slitting yarn is less compressed, and if the slitting yarn has a higher thickness while being sufficiently compressed, the porosity and an average pore size may be lowered, such that it can be difficult to three-dimensionally culture cells due to a decrease in permeability of a cell culture medium and a decrease in intracellular penetration.

Therefore, according to an exemplary embodiment of the present invention, a ratio of a basis weight to a thickness of the slitting yarn (basis weight ($g/m^2$)÷thickness (μm)) may be 1:0.8 to 1.7, and preferably 1:1 to 1.25, such that cells can be easily penetrated into the slitting yarn to more stably culture a three-dimensional cell cluster, and cultured with minimum cell death in the slitting yarn due to smooth permeation of the cell culture medium. If the ratio of a basis weight to a thickness is less than 0.8, due to an unstable surface morphology, cells can be frequently detached during culture, and when the slitting yarn has a high thickness while being sufficiently compressed, porosity and an average pore size may also be decreased such that, due to a decrease in permeability of a cell culture medium and reduced internal penetration of cells, it can be difficult to attain three-dimensional culture of the cells. In addition, if the ratio of a basis weight to a thickness is more than 1.7, the thickness of the slitting yarn may be lowered due to an excessive compression process, such that porosity and an average pore size can be reduced, and the surface morphology may become flat such that it can be difficult to stably culture cells.

In addition, the slitting yarn 200 may have a width of 0.1 to 8 mm. If slitting is performed to a width of less than 0.1 mm, cutting may not be easily performed, and cut yarns may be frequently exhibited. In addition, there is a problem in which a plurality of slitting yarns may be easily broken due to a tension and a torque applied in twisting. In addition, when slitting is performed to a width of more than 30 mm, it may be difficult to achieve a desired effect in which an irregular twist may be formed during twisting for producing yarn by braiding a plurality of slitting yarns.

In addition, the compressed nanofiber web 100 forming the slitting yarn 200 preferably may have pores with an average pore size that ensures spaces for migrating and proliferating cells, and a diameter may be determined according to a specific type of cells to be cultured. As an example, the average pore size is preferably 0.05 to 10 μm, more preferably, 10 nm to 1 μm. If the average pore size is less than 0.05 μm, the cultured cells may be parallelly migrated and proliferated on the outer surface of the compressed nanofiber web 100, rather than being migrated into pores in the compressed nanofiber web 100 during proliferation, and thus a cell cluster having a three-dimensional shape may not be cultured at a desired level. In addition, although cells are migrated into inner spaces in the compressed nanofiber web 100, a culture medium may not smoothly pass through the compressed nanofiber web 100, and therefore cells migrated into the inner spaces may die or may be inhibited in proliferation. In addition, if the average pore size is more than 10 μm, cells may be highly migrated into the inner space of the compressed nanofiber web 100 and a culture medium may be smoothly permeated. However, the cultured cells may be increased in detachment to outside the slitting yarn 200 with a culture medium passing through the compressed nanofiber web 100, and an increase in isolated culture cells is disadvantageous for culture of a cell cluster having a desired three-dimensional shape.

The scaffold fiber for forming the above-described compressed nanofiber web 100 may have an average diameter of 10 nm to 100 μm, preferably 100 nm to 50 μm, more preferably 100 nm to 10 μm, and further more preferably 100 nm to 1 μm. If the scaffold fiber has an average diameter of less than 10 nm, a mechanical strength of the fiber web may be significantly decreased, and when scaffold fiber has an average diameter of more than 100 μm, it may be difficult to form a compressed nanofiber web having porosity and a surface area of the scaffold fiber at desired levels.

Meanwhile, to three-dimensionally culture cells, the cells may be penetrated into and cultured in an inner space as well as on a surface of the compressed nanofiber web 100, and one three-dimensional cell cluster may be ultimately formed by contacting the cells penetrated into and cultured in the inner space and the cells cultured on the surface. However, even in the case of the cells cultured on the surface, three-dimensional culture of cells may be induced due to the surface morphology of the nanofiber web. As an example, the surface morphology of the compressed nanofiber web 100 consisting of the slitting yarn 200 may not be smooth, but may have irregularities, thereby having a high surface roughness. The roughness of the surface morphology of the compressed nanofiber web 100 exemplarily includes a plurality of concave and/or convex portions, and thus the cells may be more easily and firmly settled in spaces of the convex portions or grooves of the concave portions, in addition to the three-dimensional growth effect of cells, such that the number of detached cells after being loaded into the slitting yarn may be significantly reduced.

According to an exemplary embodiment of the present invention, to realize yarn for a cell culture scaffold with the above-described surface morphology for enhancing the three-dimensional growth of cells and settlement of seeded cells, the compressed nanofiber web may include a plurality of scaffold fibers, and the scaffold fibers have a diameter dispersion coefficient (E) of 8 to 25%. The diameter dispersion coefficient (E) is a parameter that can estimate how close or wide the scaffold fibers are distributed compared with a predetermined average diameter calculated in a distribution based on diameters of the scaffold fibers, and may be calculated by the following Mathematical Formula 1.

Scaffold fiber diameter dispersion coefficient (%)= [(standard deviation relative to diameters of scaffold fibers (nm)/average diameter of scaffold fibers (nm))×100    [Mathematical Formula 1]

A dispersion coefficient (%) of 0% according to Mathematical Formula 1 means that the standard deviation is 0, which means that the diameters of a plurality of scaffold fibers included in the fiber web are all equal to the average diameter. On the contrary, a gradual increase in diameter dispersion coefficient means an increase in the number of scaffold fibers with larger and/or smaller diameters than the average diameter of the plurality of scaffold fibers included in the fiber web.

The scaffold according to an exemplary embodiment of the present invention has a dispersion coefficient relative to diameters of biodegradable scaffold fibers according to Condition (1) at a predetermined average diameter that satisfies 8 to 25%, therefore, a compressed nanofiber web having an uneven surface morphology, when formed by arranging multiple concave portions and/or convex portions as described above, may be more easily implemented. However, if the dispersion coefficient is excessively large, a basis weight relative to a thickness may be increased, and therefore, the average pore size and air permeability may be greatly reduced, and due to difficult inflow of a cell culture medium into the compressed nanofiber web or exchange thereof, cell culture may be difficult to perform in the compressed nanofiber web and thus cell culture efficiency may be reduced. If the dispersion coefficient relative to a diameter is less than 8%, as the uniformity of diameters of the scaffold fibers is increased, a smooth surface morphology is likely to be expressed and the uniformity of pore sizes also increases. However, when the seeded cells are cultured two-dimensionally along the surface, rather than three-dimensionally cultured, or the average diameter of the scaffold fiber is large, a pore structure having a large average pore size is generated, such that there is a concern that the seeded cells can be detached and a three-dimensional cell cluster cannot be cultured at a desired level. In addition, if the dispersion coefficient relative to a diameter is more than 25%, in a compressed nanofiber web having a slightly smaller average diameter, due to increased non-uniformity of the scaffold diameter, the average pore size of the compressed nanofiber web is very small, and therefore inflow of a cell culture medium into the compressed nanofiber web or exchange thereof may be difficult, and cells may be cultured along the surface, rather than cultured three-dimensionally.

In addition, the air permeability of a compressed nanofiber web may be 1 to 10 cfm. One of the major factors for three-dimensionally growing cells in slitting yarn serving as a scaffold for cell culture is whether materials required for cell culture can be continuously and actively supplied. If cells are three-dimensionally grown on the surface of slitting yarn, it may be difficult to actively contact cells, which are placed adjacent to the surface of the slitting yarn or cells cultured after penetration and settlement of the cells in an inner space of the slitting yarn, with a cell culture medium, compared with cells located to be exposed at an outer space. Therefore, for active inflow and outflow of the cell culture medium into the compressed nanofiber web, the compressed nanofiber web may have an air permeability of 1 to 10 cfm. If the air permeability is less than 1.0 cfm, it may be difficult for cells to be penetrated into a scaffold, and a component capable of dissolving a cell culture medium or a biodegradable component may not be smoothly permeated. In addition, if the air permeability is more than 10 cfm, a mechanical strength of the nanofiber web may be too low to form slitting yarn, or a fiber web having significantly high diameter of the scaffold fiber and/or having significantly high thickness may be formed, and therefore the weight of the scaffold may increase, it may be difficult for the fiber web to be applied to an incubator with a limited, small volume, and it may be difficult to culture the seeded cells in a desired amount due to detachment of the cells.

In addition, the compressed nanofiber web 100 may have a porosity of 40 to 90%, and therefore a cell cluster with a three-dimensional shape may be more easily formed using cells migrated into and proliferated in the compressed nanofiber web 100, a culture medium may be contained in pores of the compressed nanofiber web 100, and permeability of the culture medium may be enhanced. If the porosity is less than 40%, it may be difficult to form a cell cluster with a three-dimensional shape, and the cells migrated into and proliferated in the compressed nanofiber web 100 may die. In addition, if the porosity is more than 90%, due to a decrease in mechanical strength of the scaffold, the scaffold may be disrupted during cell culture.

The above-described scaffold fiber may be formed of a known fiber-forming component to be formed in the form of a fiber, and since a material may vary depending on a specific purpose, for example, requirement of a decomposition property, the present invention is not particularly limited thereto. The fiber-forming component may include a cellulose component such as cotton or hemp, a protein component such as wool or silk, or a natural fiber component such as a mineral component. In addition, the fiber-forming component may be a known artificial fiber component.

Meanwhile, the fiber-forming component may include any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly(alkylene oxide), a poly(amino acid), a poly(allylamine), polyphosphazene and a polyethyleneoxide-polypropyleneoxide block copolymer, or any one or more biodegradable components selected from the group consisting of polycaprolactone, polydioxanone, polyglycolic acid, poly (L-lactide) (PLLA), poly(DL-lactide-co-glycolide) (PLGA), polylactic acid and polyvinyl alcohol depending on purpose.

In addition, the above-described compressed nanofiber web 100, more particularly, a scaffold fiber for forming the nanofiber web 100 may further include a functional material in addition to the fiber-forming component.

Cell culture technology that has been recently studied is developed for in vitro realization of an intercellular environment of an actual body, and to create a cell culture environment similar to the intercellular environment in the body, various components included in the extracellular matrix in the body tend to be contained in a culture medium in in vitro culture. However, when a material that can promote cell culture is contained in a culture medium, there is a limitation to continuous exposure of the material to cells that are being cultured, and for continuous exposure, a content of the material has to be increased in the culture medium, but there are problems in cost and proliferation efficiency. Accordingly, since a physiologically active component is included in slitting yarn by being fixed on the surface of the scaffold fiber included in the nanofiber web according to an exemplary embodiment of the present invention, cell proliferation may be more accelerated by stabilizing adhesion of the physiologically active component to the cultured cells located on the scaffold fiber or in spaces around the scaffold fiber, and sustaining and amplifying cell stimulation and intracellular signal transduction thereby.

The physiologically active component may be a component inducing one or more of adhesion, migration, growth, proliferation and differentiation of cells.

First, an adhesive physiologically active component, which is a component of the physiologically active components, which enhances cell adhesion, may serve to fix cells to be cultured on a cell scaffold at an early stage to prevent suspension of the cells in a culture medium, and/or to fix a non-adhesive physiologically active component involved in the migration, growth, proliferation and differentiation of cells to a scaffold fiber to prevent detachment of the non-adhesive physiologically active component from the scaffold fiber during cell culture on the scaffold fiber. The adhesive physiologically active component may be any known adhesive component that does not exhibit cytotoxicity because it has conventional biocompatibility, without limitation, and preferably includes one or more types selected from the group consisting of proteins comprising 1 to 20 repeats of amino acids of SEQ ID NOs: 1 to 7 and proteins produced by fusing at least two thereof, and therefore there are advantages in which cytotoxicity can be considerably decreased, a high adhesive strength to the non-adhesive physiologically active component can be exhibited, and release of the non-adhesive physiologically active component which is fixed and isolation of cells, which occur by dissolving the adhesive physiological active component in a culture medium during cell culture, can be prevented.

Subsequently, among physiologically active components which can be included in the nanofiber web, non-adhesive physiologically active components directly/indirectly inducing any one or more of migration, growth, proliferation and differentiation of cells to improve cell culture may be any known material that expresses the above-described function without limitation.

For example, the physiologically active component may include any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell. Here, the monoamine includes, for example, a compound including a primary amine such as catecholamine or indole amine. In addition, the peptide may include an oligopeptide, and the protein may include a polypeptide, for example, fibronectin. The saccharide may include a monosaccharide, a polysaccharide, an oligosaccharide, and a carbohydrate. In addition, the lipid may be, for example, a steroid hormone.

Meanwhile, the physiologically active component may include a motif. The motif may be a natural or recombinant peptide comprising a predetermined amino acid sequence included in any one or more selected from proteins, glucoproteins and proteoglycans included in a growth factor or the ECM. Specifically, the motif may include a predetermined amino acid sequence included in any one or more growth factors (GFs) selected from the group consisting of adrenomedullin, angiopoietin, a bone morphogenetic protein (BMP), a brain-derived neurotrophic factor (BDNF), an epithelial growth factor (EGF), erythropoietin, a fibroblast growth factor, a glial cell line-derived neurotrophic factor (GDNF), a granulocyte colony-stimulating factor (G-CSF), a granulocyte macrophage colony-stimulating factor (GM-CSF), growth differentiation factor-9 (GDF9), a hepatocytic growth factor (HGF), a hepatoma-derived growth factor (HDGF), an insulin-like growth factor (IGF), a keratinocyte growth factor (KGF), a migration-stimulating factor (MSF), myostatin (GDF-8), a nerve growth factor (NGF), a platelet-derived growth factor (PDGF), thrombopoietin (TPO), a T-cell growth factor (TCGF), neuropilin, transforming growth factor-α (TGF-α), transforming growth factor-β (TGF-β), tumor necrosis factor-α (TNF-α), a vascular endothelial growth factor (VEGF), IL-1, IL-2, IL-3, IL-4, IL-5, IL-6 and IL-7. Alternatively, the motif may include a predetermined amino acid sequence included in any one or more selected from the group consisting of hyaluronic acid, heparin sulfate, chondroitin sulfate, dermatan sulfate, keratan sulfate, alginate, fibrin, fibrinogen, collagen, elastin, fibronectin, bitronectin, carderine and laminin in the ECM. In addition, the motif may include both of a predetermined amino acid sequence included in the growth factor and a predetermined amino acid sequence included in the ECM. More preferably, the motif may include one or more selected from the group consisting of proteins comprising amino acid sequences of SEQ. ID. NOs: 8 to 28 and one or more selected from the group consisting of proteins in which at least two of the proteins are fused, but the present invention is not limited thereto.

Meanwhile, the motif may be integrated with the above-described adhesive component by a covalent bond. For example, when the adhesive component is a protein, the motif may be covalently bonded to the N-terminus and/or the C-terminus of a polypeptide directly or via a heterologous peptide or polypeptide, and in this case, the physiologically active component may be more tightly adhered to a scaffold fiber, and release of the physiologically active component during cell culture may be minimized.

Figure 3:
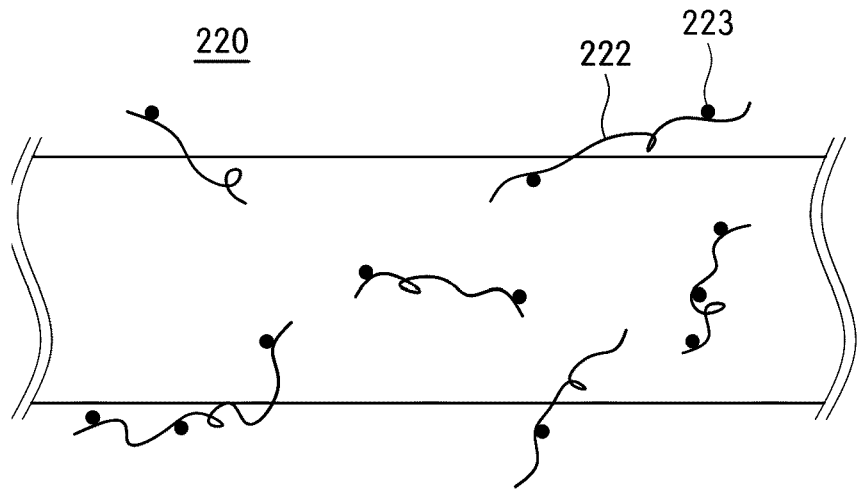
FIG. 3 is a cross-sectional view of a physiologically active component fixed on a nanofiber forming slitting yarn included in an exemplary embodiment of the present invention.

The above-described adhesive physiologically active component and non-adhesive physiologically active component may be included by being fixed to a scaffold fiber, and according to a method of fixing these components shown in FIG. 3, a part of an adhesive physiologically active component 222 is located in the scaffold fiber 220, and the remaining part is located outside and fixed on the surface of the scaffold fiber 220. A non-adhesive physiologically active component 223 may be bonded onto the fixed adhesive physiologically active component 222 and thus also fixed on the scaffold fiber 220. However, unlike FIG. 3, an adhesive physiologically active component may not be included in the scaffold fiber 220, and the adhesive physiologically active component may be fixed onto a region of the outer surface by adhesion or may cover the entire outer surface of the scaffold fiber 220, but the present invention is not limited thereto.

In addition, the yarn for a cell culture scaffold according to an exemplary embodiment of the present invention may include one or multiple strands of the above-described slitting yarns as a mono-fiber, and when the multiple strands are included, they may be braided and then twisted. In addition, as a mono-fiber, in addition to the above-described slitting yarn, a different type of yarn which can enhance a mechanical strength of the yarn for a cell culture scaffold may be further included, and the different type of yarn may be spun yarn or filament yarn which is formed of a known material.

The yarn for a cell culture scaffold according to the present invention including the above-described slitting yarn 200 may be produced by a production method to be described below. However, the present invention is not limited to the following production method.

Figure 4:
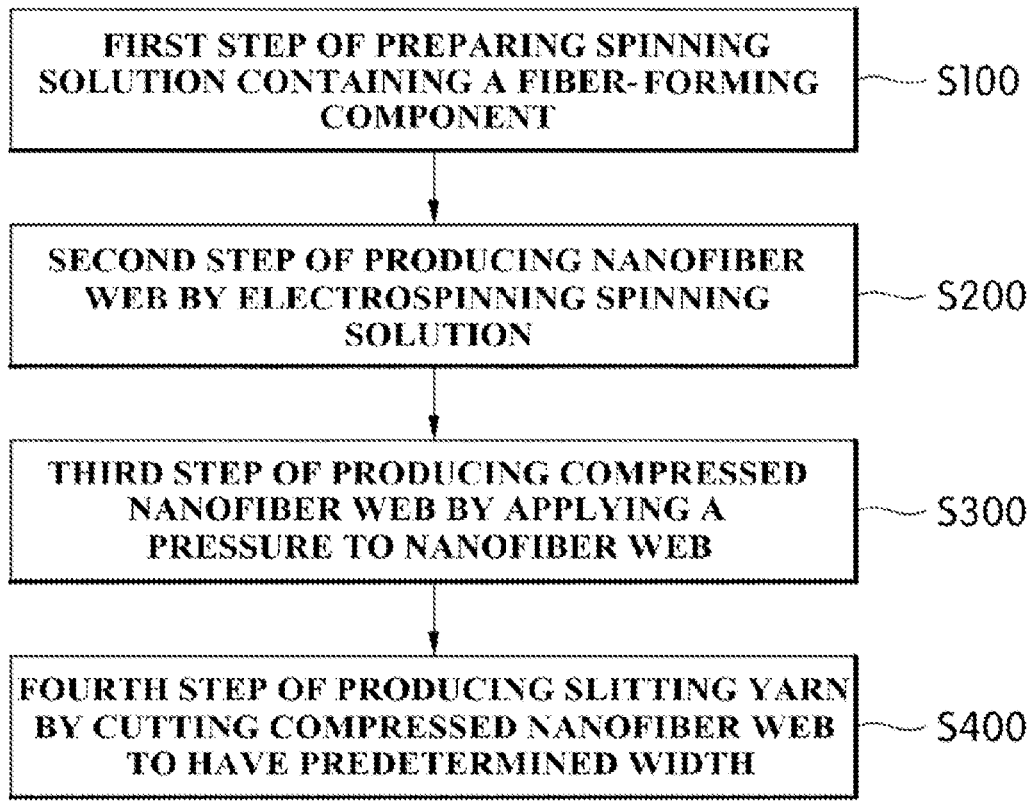
FIG. 4 is a flowchart illustrating a method of producing yarn for a cell culture scaffold according to an exemplary embodiment of the present invention.

As shown in FIG. 4, the yarn for a cell culture scaffold including the slitting yarn 200 according to an exemplary embodiment of the present invention may be produced by a first step of preparing a spinning solution containing a fiber-forming component (S100), a second step of producing a nanofiber web 10 by electrospinning the spinning solution (S200), a third step of producing a compressed nanofiber web 100 by applying a pressure to the nanofiber web 10 (S300), and a fourth step of producing slitting yarn 200 by cutting the compressed nanofiber web 100 to have a predetermined width (S400).

First, in the first step (S100), a spinning solution may include a solvent in addition to a fiber-forming component.

The solvent may be any one that is used in preparation of an electrospinning solution and can dissolve the above-described fiber-forming component without limitation. In addition, if the second step which will be described below is dry spinning, a solvent that can be easily evaporated is preferably selected. Since the type of the solvent can be selected according to the type of a specifically selected fiber-forming component specifically selected, the present invention is not particularly limited to a specific type of the solvent. In one example, the solvent may be any one or more selected from the group consisting of diethyl carbonate (DEC), dimethyl carbonate (DMC), ethyl methyl carbonate (EMC), propylene carbonate (PC), water, acetic acid, formic acid, chloroform, dichloromethane, acetone, 1,1,1,3,3,3-hexafluoro-2-propanol (HFIP) and isopropyl alcohol.

In the preparation of the spinning solution, it is suitable that the fiber-forming component is contained at approximately 5 to 50 wt %. If the content is less than 5 wt %, it is difficult to form a nanofiber web 10 by spraying the spinning solution onto beads, rather than fabricating the nanofiber web 10 itself, and if the content is more than 50 wt %, it is difficult to form a fiber due to a poor spinning property caused by a very high viscosity of the spinning solution. Therefore, the spinning solution is prepared at a concentration at which a fibrous structure is easily formed to control a fiber morphology.

The spinning solution may be prepared by mixing the fiber-forming component and the solvent to have a viscosity of 50 to 3000 cps. If the viscosity of the spinning solution is less than 50 cps, due to high flowability of the spinning solution, it is difficult to produce a nanofiber web 10 by spraying liquid drops from a nozzle of a sprayer, and when the viscosity of the spinning solution is more than 3000 cps, the flowability of the spinning solution may be lowered and thus the spinning property may be decreased.

Meanwhile, the spinning solution may further include an additive included in a conventional scaffold for cell culture or scaffold for tissue engineering, and for example, the additive may be a hydrophilicity-enhancing component such as a non-ionic surfactant. Other than this, the additive may be a known one selected according to purpose, and therefore, in the present invention, descriptions of the additive will be omitted.

Figure 5:
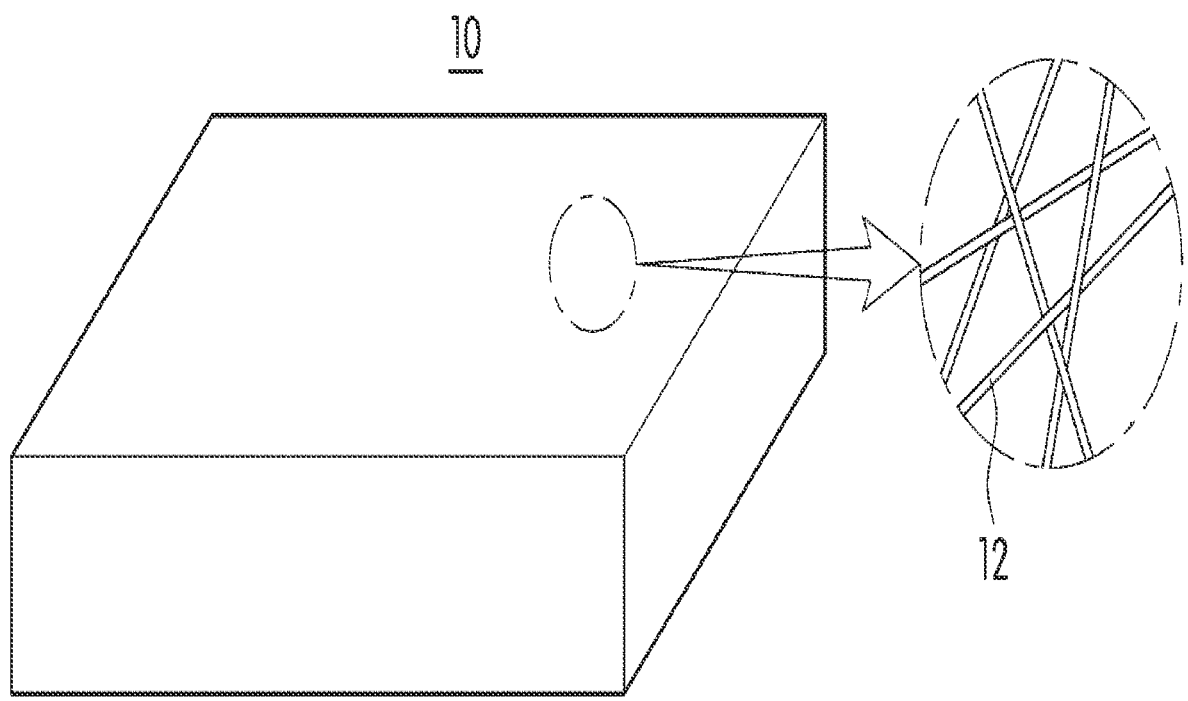
FIG. 5 shows a perspective view and a partial enlargement of a nanofiber web produced in a second step of a production method according to an exemplary embodiment of the present invention.

Subsequently, the second step (S200) of producing a nanofiber web 10 as shown in FIG. 5 by electrospinning the above-described spinning solution is performed.

The step 2 (S200) may be accomplished using a conventional electrospinning device, and the electrospinning device may include a solution tank storing a spinning solution, and a spinning pack in which a plurality of spinning nozzles are linked to a high-voltage generator and arranged in a grid form. Meanwhile, a collector may be included under the spinning pack to collect a fiber mat in which radiating scaffold fibers are accumulated, and the collector may collect a continuous fiber mat having a predetermined thickness, which is located on a conveyer belt and sequentially formed. Here, as an external solidification solution is contained in the collector, the spun scaffold fibers may be solidified, or the spun scaffold fibers may be solidified in air or with separate cooling wind without an external solidification solution, and then the solidified scaffold fibers may be collected by the collector.

The collected scaffold fiber mat may be subjected to a drying process for evaporating the remaining solvent and the external solidification solution, and thereby the nanofiber web 10 may be produced.

The produced nanofiber web 10 may be also subjected to plasma treatment, coating of the surface of the scaffold fiber with dopamine, etc. to enhance hydrophilicity.

In addition, the produced nanofiber web 10 may be further subjected to an extension process in a specific direction for control of a pore size and orientation of the fiber-forming component forming the nanofiber. In addition, the nanofiber web 10 may be further subjected to a process of applying heat and/or pressure to deepen a three-dimensional network structure and satisfy a basis weight with respect to a desired thickness, and this process may be a conventional calendering process. In addition, a process of forming a separate adhesive layer on one surface of the produced nanofiber web 10, for example, an edge of the fiber web may be further performed to fix or adhere the fiber web onto a culture container.

Subsequently, in the third step (S300), a process of producing a compressed nanofiber web 100 by applying a pressure to the nanofiber web 10 is performed.

The compressed nanofiber web 100 may be produced by compressing the produced nanofiber web 10 by various methods including compression, rolling, thermal bonding, ultrasonic bonding, etc. In the present invention, the compression process is for forming the nanofiber web 10 in a film form by compression-fixing individual spun fibers by thermal or ultrasonic treatment. The third step (S300) is preferably carried out in a temperature range of 20 to 250° C., and more preferably, 80 to 160° C., in which the fiber-forming component does not melt, and under a pressure of 3 to 5 kPa. When the temperature is less than 20° C., the thermal treatment temperature is too low to stably perform bonding between the nanofibers 12. In addition, in the case of a fiber forming component having a high glass transition temperature, bonding between the nanofibers 12 is hardly performed, and thus it is highly likely that slitting will not be performed smoothly in the subsequent process of producing the slitting yarn 200. In addition, when the thermal treatment temperature is more than 250° C., it is not preferable in that there is a high possibility of losing a fibrous structure due to a melt fiber-forming component constituting the nanofiber 12. At this time, elongation can also be performed by thermal treatment.

Subsequently, in the fourth step (S400), a process of producing slitting yarn 200 by cutting the compressed nanofiber web 100 to have a predetermined width is performed.

Slitting yarn 200 consisting of scaffold fiber 220 is produced by slitting the compressed nanofiber web 100 to a width of 0.1 to 8 mm according to various methods using a cutter or slitter.

Afterward, a twisting process may be performed by braiding one or several strands of the produced slitting yarns. The twisted yarn following braiding may have a mechanical strength higher than the one strand of slitting yarn, and therefore may be advantageous for stable culture of cells.

Meanwhile, the present invention may provide a fabric for cell culture using the yarn according to the present invention or ply yarn thereof.

The fabric may be any one of a woven fabric, a knitted fabric and a non-woven fabric, and the type of the fabric may vary depending on purpose. The woven fabric, knitted fabric and non-woven fabric may be produced by known corresponding methods. For example, the woven fabric may be a twill fabric produced by diagonally weaving any one or more of the above-described yarn, ply yarn as any one or more of a warp and weft. In addition, the knitted fabric may be a flat knit fabric weft-knitted by putting the above-described yarn, ply yarn into a flat knitting machine. In addition, the non-woven fabric may be produced by adding an adhesive component to short-cut yarn formed by cutting the yarn, combination yarn and/or ply yarn to a predetermined fiber length and applying heat/pressure thereto.

In addition, the present invention may provide a graft for tissue engineering or a cell incubator, which includes a cell cluster cultured by grafting cells to be cultured on the above-described yarn or fabric according to the present invention. Here, the cells to be cultured may be cultured and proliferated in a region including a surface and an inner space of a nanofiber web of the yarn, which is the slitting yarn. In addition, the cell cluster may include any one or more types of stem cells selected from the group consisting of totipotent stem cells, pluripotent stem cells, multipotent stem cells, oligopotent stem cells and single stem cells, and/or one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

TABLE 2

| SEQ. ID. NO: | Amino acid sequence |
|---|---|
| 1 | Met Ala Lys Pro Ser Tyr Pro Pro Thr Tyr |
|  | Lys Ala Lys Pro Ser Tyr Pro Pro Thr Tyr |
|  | Lys Ala Lys Pro Ser Tyr Pro Pro Thr Tyr |
|  | Lys Ala Lys Pro Ser Tyr Pro Pro Thr Tyr |
|  | Lys Ala Lys Pro Ser Tyr Pro Pro Thr Tyr |
|  | Lys Ala Lys Pro Ser Tyr Pro Pro Thr Tyr |
|  | Lys Ser Ser Glu Glu Tyr Lys Gly Gly Tyr |
|  | Tyr Pro Gly Asn Thr Tyr His Tyr His Ser |
|  | Gly Gly Ser Tyr His Gly Ser Gly Tyr His |
|  | Gly Gly Tyr Lys Gly Lys Tyr Tyr Gly Lys |
|  | Ala Lys Lys Tyr Tyr Tyr Lys Tyr Lys Asn |
|  | Ser Gly Lys Tyr Lys Tyr Leu Lys Lys Ala |
|  | Arg Lys Tyr His Arg Lys Gly Tyr Lys Lys |
|  | Tyr Tyr Gly Gly Ser Ser Ala Lys Pro Ser |
|  | Tyr Pro Pro Thr Tyr Lys Ala Lys Pro Ser |
|  | Tyr Pro Pro Thr Tyr Lys Ala Lys Pro Ser |
|  | Tyr Pro Pro Thr Tyr Lys Ala Lys Pro Ser |
|  | Tyr Pro Pro Thr Tyr Lys Ala Lys Pro Ser |
|  | Tyr Pro Pro Thr Tyr Lys Ala Lys Pro Ser |
|  | Tyr Pro Pro Thr Tyr Lys |

TABLE 2-continued

| SEQ. ID. NO: | Amino acid sequence |
|---|---|
| 2 | Met Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ser Ser Glu Glu Tyr Lys Gly Gly Tyr<br>Tyr Pro Gly Asn Thr Tyr His Tyr His Ser<br>Gly Gly Ser Tyr His Gly Ser Gly Tyr His<br>Gly Gly Tyr Lys Gly Lys Tyr Tyr Gly Lys<br>Ala Lys Lys Tyr Tyr Lys Tyr Lys Asn<br>Ser Gly Lys Tyr Lys Tyr Leu Lys Lys Ala<br>Arg Lys Tyr His Arg Lys Gly Tyr Lys Lys<br>Tyr Tyr Gly Gly Ser Ser Ala Lys Pro Ser<br>Tyr Pro Pro Thr Tyr Lys Ala Lys Pro Ser<br>Tyr Pro Pro Thr Tyr Lys Ala Lys Pro Ser<br>Tyr Pro Pro Thr Tyr Lys Ala Lys Pro Ser<br>Tyr Pro Pro Thr Tyr Lys Ala Lys Pro Ser<br>Tyr Pro Pro Thr Tyr Lys Ala Lys Pro Ser<br>Tyr Pro Pro Thr Tyr Lys Gly Arg Gly Asp<br>Ser Pro |
| 3 | Met Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Pro Trp Ala Asp Tyr Tyr Gly Pro Lys<br>Tyr Gly Pro Pro Arg Arg Tyr Gly Gly Gly<br>Asn Tyr Asn Arg Tyr Gly Arg Arg Tyr Gly<br>Gly Tyr Lys Gly Trp Asn Asn Gly Trp Lys<br>Arg Gly Arg Trp Gly Arg Lys Tyr Tyr Gly<br>Ser Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Ala Lys Pro Ser Tyr Pro Pro Thr Tyr<br>Lys Leu |
| 4 | Ala Asp Tyr Tyr Gly Pro Lys Tyr Gly Pro<br>Pro Arg Arg Tyr Gly Gly Gly Asn Tyr Asn<br>Arg Tyr Gly Arg Arg Tyr Gly Gly Tyr Lys<br>Gly Trp Asn Asn Gly Trp Lys Arg Gly Arg<br>Trp Gly Arg Lys Tyr Tyr |
| 5 | Ser Ser Glu Glu Tyr Lys Gly Gly Tyr Tyr<br>Pro Gly Asn Thr Tyr His Tyr His Ser Gly<br>Gly Ser Tyr His Gly Ser Gly Tyr His Gly<br>Gly Tyr Lys Gly Lys Tyr Tyr Gly Lys Ala<br>Lys Lys Tyr Tyr Lys Tyr Lys Asn Ser<br>Gly Lys Tyr Lys Tyr Leu Lys Lys Ala Arg<br>Lys Tyr His Arg Lys Gly Tyr Lys Lys Tyr<br>Tyr Gly Gly Gly Ser Ser |
| 6 | Ala Lys Pro Ser Tyr Pro Pro Thr Tyr Lys |
| 7 | Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys<br>Ala Lys Pro Ser Tyr Pro Pro Thr Tyr Lys |
| 8 | Arg Gly Asp |
| 9 | Arg Gly Asp Ser |
| 10 | Arg Gly Asp Cys |
| 11 | Arg Gly Asp Val |
| 12 | Arg Gly Asp Ser Pro Ala Ser Ser Lys Pro |
| 13 | Gly Arg Gly Asp Ser |
| 14 | Gly Arg Gly Asp Thr Pro |
| 15 | Gly Arg Gly Asp Ser Pro |
| 16 | Gly Arg Gly Asp Ser Pro Cys |
| 17 | Tyr Arg Gly Asp Ser |
| 18 | Ser Pro Pro Arg Arg Ala Arg Val Thr |
| 19 | Trp Gln Pro Pro Arg Ala Arg Ile |
| 20 | Asn Arg Trp His Ser Ile Tyr Ile Thr Arg Phe Gly |
| 21 | Arg Lys Arg Leu Gln Val Gln Leu Ser Ile Arg Thr |
| 22 | Lys Ala Phe Asp Ile Thr Tyr Val Arg Leu Lys Phe |
| 23 | Ile Lys Val Ala Asn |
| 24 | Lys Lys Gln Arg Phe Arg His Arg Asn Arg Lys Gly Tyr Arg Ser Gln |
| 25 | Val Ala Glu Ile Asp Gly Ile Gly Leu |
| 26 | Pro His Ser Arg Asn Arg Gly Asp Ser Pro |
| 27 | Asn Arg Trp His Ser Ile Tyr Ile Thr Arg Phe Gly |
| 28 | Thr Trp Tyr Lys Ile Ala Phe Gln Arg Asn Arg Lys |

EXAMPLES

Hereinafter, the present invention will be described in further detail with reference to examples. The examples are merely provided to more fully describe the present invention, and it will be obvious to those of ordinary skill in the art that the scope of the present invention is not limited to the following examples.

Example 1

Figure 6B:
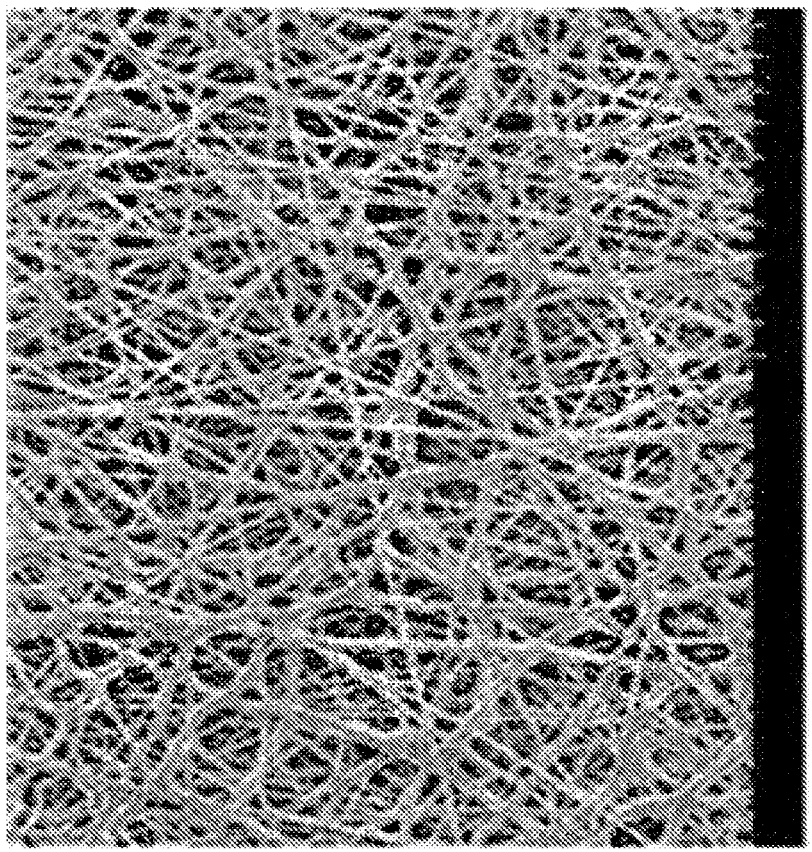
FIGS. 6A-6B show an image of a 1.7M wide nanofiber web for producing slitting yarn included in an exemplary embodiment of the present invention (FIG. 6A) and a scanning electron microscope image of the slitting yarn (FIG. 6B).
Figure 6A:
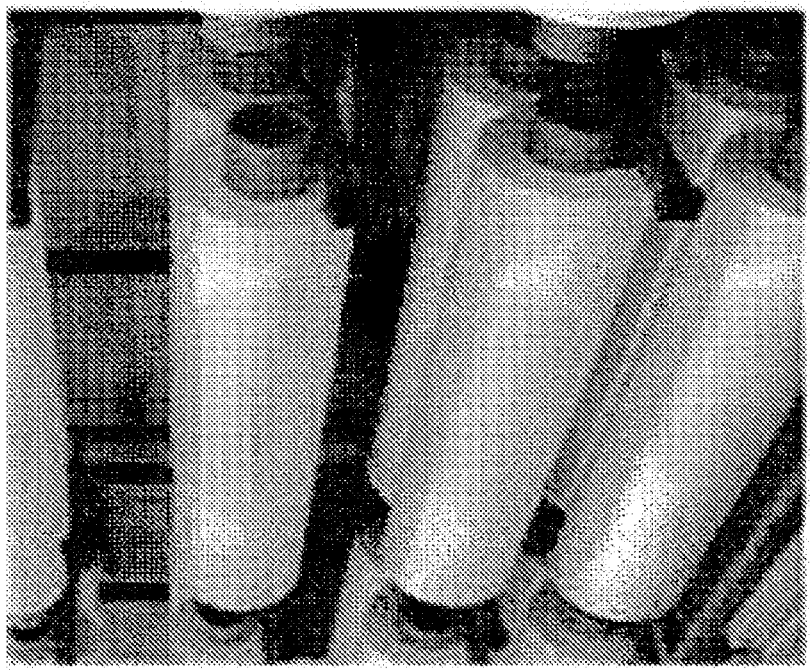

First, to prepare a spinning solution, 12 g of polyvinylidene fluoride (Arkema, Kynar761) as a fiber-forming component was dissolved in 88 g of a mixed solvent prepared by mixing dimethylacetamide and acetone at a weight ratio of 70:30 using a magnetic bar at 80° C. for 6 hours, thereby preparing a mixed solution. A nanofiber web formed of a scaffold fiber with a diameter distribution as shown in Table 1 below was obtained by electrospinning of the prepared spinning solution using an electrospinning device under conditions of an applied voltage of 25 kV, a distance between a current collector and a spinning nozzle of 25 cm and a discharge amount of 0.05 ml/hole under an environment of an R.H. 65% and 30° C. The obtained nanofiber web was calendered twice at 130° C. and under a pressure of 4 kPa, thereby producing a compressed nanofiber web which has a three-dimensional network structure as shown in FIG. 6B, a basis weight of 10 g/m² and a thickness of 10 μm, and the produced compressed nanofiber web was wrapped around a roll as shown in FIG. 6A.

Figures 7A, 7B, 7C:
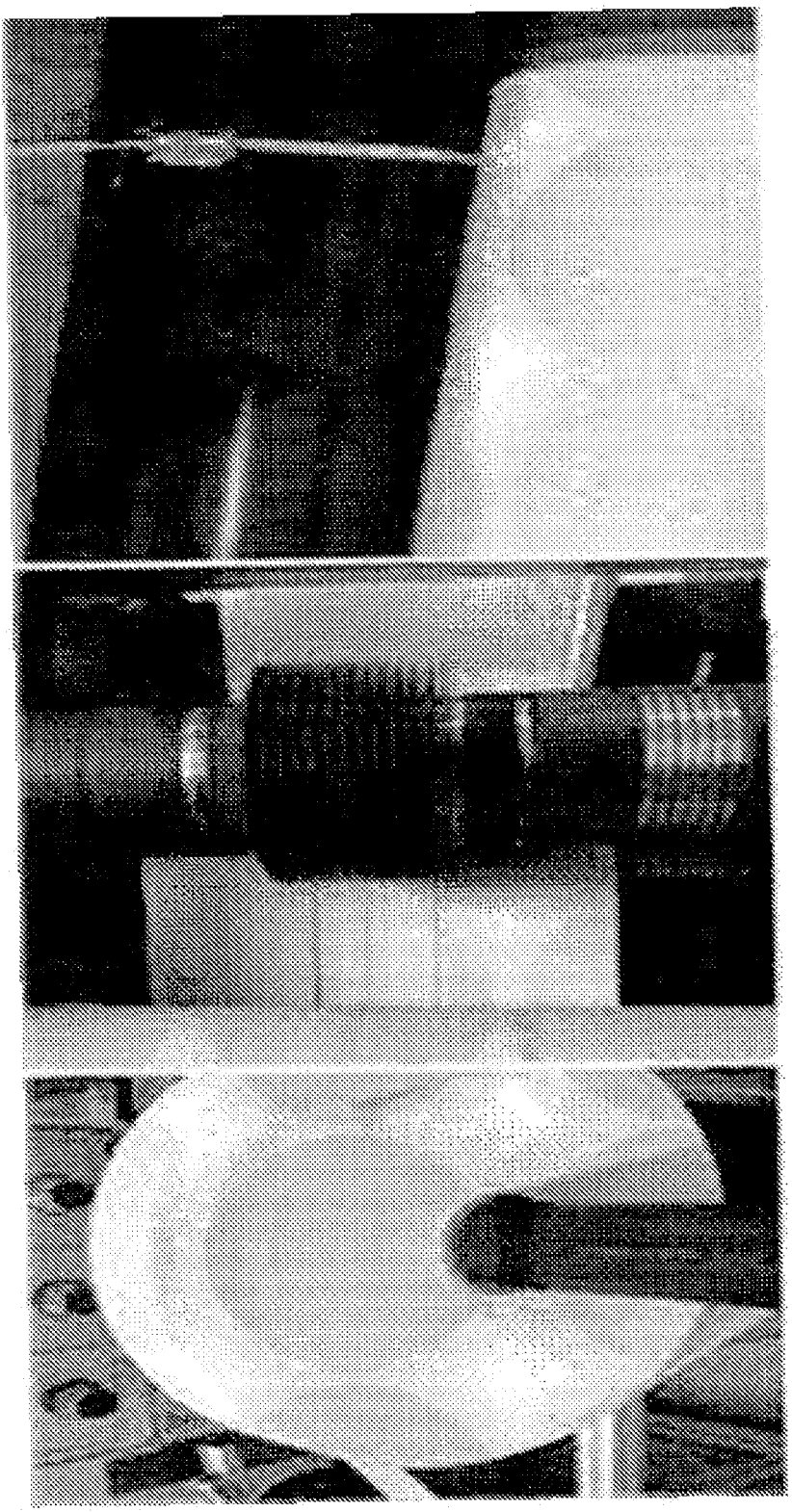

Afterward, the roll of the compressed nanofiber web was first-slit to have a width of 5 mm as shown in FIG. 7A, and second-precision slit to have a width of 1.5 mm as shown in FIG. 7B, thereby obtaining slitting yarn, and an image of wrapped slitting yarn produced by the second precision slitting is shown in FIG. 7C. The produced slitting yarn had a width of 1.5 mm.

Example 2 to 6

Slitting yarns were produced as shown in Table 3 below by the same method as described in Example 1, except that a compressed nanofiber web was produced to have a basis weight and a thickness as shown in Table 3 below by controlling the basis weight/thickness of a nanofiber web before compression and the intensity of a pressure in compression.

Comparative Example 1

Slitting yarn was produced as shown in Table 3 by the same method as described in Example 1, except that a nanofiber web has a thickness of 12.5 μm and a basis weight of 8 g/m² without compression.

Experimental Example 1

A diameter distribution of scaffold fibers in the nanofiber web with respect to the nanofiber web before slitting in Examples and the comparative example was measured.

Specifically, an average diameter and the standard deviation of the diameter of the scaffold fiber were calculated using the diameter distribution of the scaffold fibers measured by a method according to a fiber diameter program (developed by AMOGREENTECH Co., Ltd.), and the average diameter and dispersion coefficient are shown in Table 3.

Experimental Example 2

Air permeability was measured for a nanofiber web before slitting in Examples and the comparative example, and the result is shown in Table 3 below.

The air permeability was determined using a device produced using TEXTEST instruments after cutting the fiber web to a test area of 38 cm² to be placed in the device, and blowing air at a test pressure of 125 Pa to measure an amount of air passing through the fiber web, and the unit of the air permeability was cfm (ft3/ft2/min).

Experimental Example 3

The slitting yarns prepared in Examples and Comparative Examples were cut to the same length, and fixed on a well plate for cell culture. Fibroblasts (HS27) were loaded into the prepared well plate, and proliferated in a 10% complete medium at 37° C. for 4 days. Here, the 10% complete medium was prepared by mixing Ham's F12 medium with Dulbecco's Modified Eagle Medium (DMEM) at a volume ratio of 1:1.5, and adding 7 vol % of fetal bovine serum, 65 U/mL of penicillin and 65 μg/mL of streptomycin.

Afterward, DAPI staining was performed on the proliferated fibroblasts, and the surface and inner space were visualized by confocal microscopy in an upward Z-axis direction while the cultured cells were adhered to the slitting yarns, the number of cells cultured on the surface of the slitting yarn (the average of the number of cells on a top surface and the number of cells on a bottom surface) and the number of cells cultured in the slitting yarn (the mean value of the numbers of cells slitting yarn at the ⅓ spot and the ⅔ spot of the thickness of the cross-section) were measured and calculated. Here, Table 3 below shows the numbers of cells in Examples 2 to 6 and the comparative example, relative to the numbers of cells on a surface of and in the slitting yarn in Example 1, which was set to 100%. In addition, FIGS. 8 and 9 show cross-sections of specimens of Examples 1 and 2, measured by height.

Figure 8:
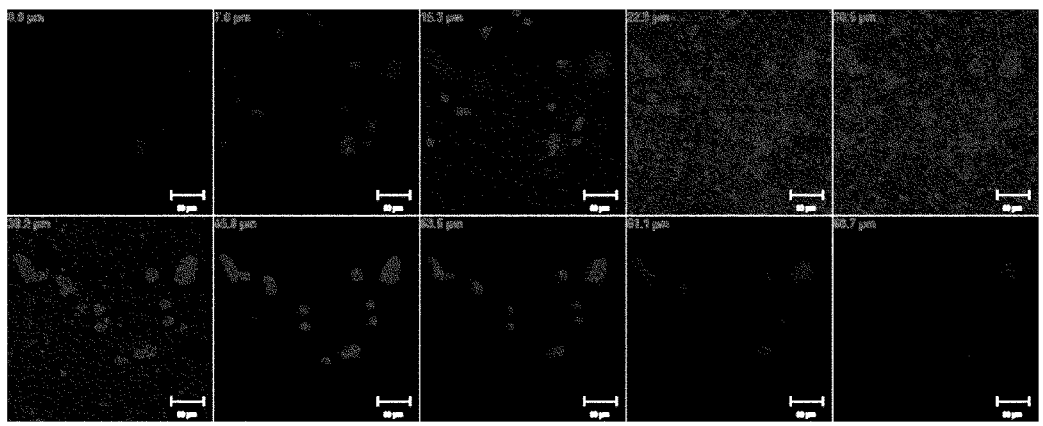
FIGS. 8 and 9 show images taken using a confocal microscope by height of a specimen in a vertically upward direction while a cell cluster is adhered in the cell cluster specimen culture in slitting yarn according to an exemplary embodiment of the present invention.

Specifically, in FIG. 8, it can be confirmed that, the cells were observed first at a height of 7.6 μm by observing the samples vertically upward, and cultured to form multiple cell clusters at a height of 15.3 μm. In addition, as the cultured cell cluster and the nanofiber web formed of a scaffold fiber were observed at a height of 22.9 μm, it can be expected that the height of the bottom surface of the slitting yarn is present between 15.3 to 22.9 μm. In addition, it can be confirmed that a large amount of cell clusters were cultured even at a height of 38.5 μm, and a large amount of cell clusters were cultured even at heights of 38.2 to 45.8 μm, which were higher than the top surface of the slitting yarn, and therefore, it can be confirmed that cells were three-dimensionally cultured evenly in and on the surface of the slitting yarn according to Example 1.

Figure 9:
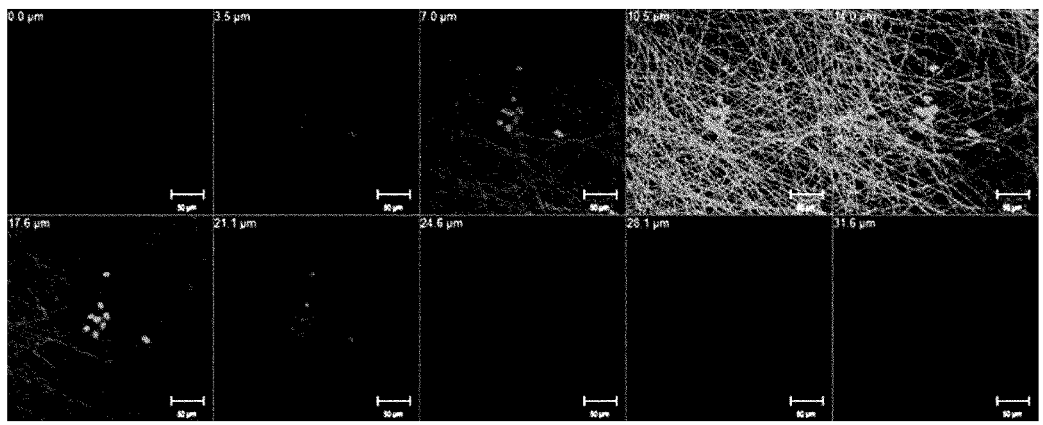

Meanwhile, in FIG. 9, it can be confirmed that cells were observed at a height of 3.5 μm, and cultured close to the surface and in the slitting yarn at a height ranging from 7.0 to 17.6 μm. However, the amount and size of the cultured cell clusters are significantly smaller than those shown in FIG. 8.

TABLE 3

| | Example 1 | Example 2 | Example 3 | Example 4 | Example 5 | Example 6 | Comparative Example 1 |
|---|---|---|---|---|---|---|---|
| Average diameter of scaffold fiber (nm) | 402 | 400 | 400 | 404 | 401 | 402 | 400 |
| Dispersion coefficient of scaffold fiber (%) | 13.25 | 13.01 | 14.9 | 12.3 | 15.1 | 14.21 | 13.25 |
| Basis weight (g/m²) | 10 | 19 | 10 | 10 | 9.5 | 9 | 8 |
| Thickness (μm) | 10 | 10.8 | 6.2 | 8 | 11.2 | 12.0 | 12.5 |
| Basis weight (g/m²)/thickness (μm) | 1 | 1.76 | 1.61 | 1.25 | 0.85 | 0.75 | 0.64 |
| Average pore size (nm) | 500 | 430 | 458 | 472 | 519 | 538 | 565 |
| Air permeability (cfm) | 2.0 | 1.7 | 1.8 | 1.9 | 2.1 | 2.1 | 2.3 |
| Surface cell number (%) | 100 | 73 | 85 | 93 | 90 | 78 | 53 |
| Inner cell number (%) | 100 | 61 | 80 | 92 | 83 | 80 | 55 |

As shown in Table 3, it can be seen that since the slitting yarn of Comparative Example 1 produced using a nanofiber web before compression was structurally unstable, cells were easily detached and difficult to stably culture such that the number of cultured cells was significantly smaller than those of the examples.

In addition, it can be confirmed that the slitting yarns according to Examples 1, 3, 4 and 5 having suitable basis weight and thickness among the examples are more suitable as a scaffold for cell culture, compared with the slitting yarns according to Examples 2 and 6.

Embodiments of the present invention have been described above, but the spirit of the present invention is not limited to the embodiments presented herein, and it will be understood by those of ordinary skill in the art that other embodiments may be easily suggested by adding, changing, deleting or adding components within the scope of the same idea and are also included in the scope of the spirit of the present invention.

The invention claimed is:

1. A yarn for a cell culture scaffold, comprising:
a slitting yarn having a three-dimensional network structure formed by randomly arranging and stacking a plurality of scaffold fibers, and having a predetermined width and thickness,
wherein a diameter dispersion coefficient (E) of the scaffold fibers in a diameter distribution of the scaffold fibers is 12.3 to 13.25% and an average diameter of the plurality of scaffold fibers is 402 to 404 nm, and
wherein the slitting yarn has a basis weight of 7 to 30 g/m$^2$, a thickness of 8 to 10 μm, a ratio of the basis weight to the thickness of 1:1.0 to 1.25, an air permeability of 1.9 to 2.0 cfm, and an average pore size of 472 to 500 nm.

2. The yarn according to claim 1, wherein the yarn has a twisted form.

3. The yarn according to claim 1, wherein the scaffold fibers are formed of any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly(alkylene oxide), a poly (amino acid), a poly(allylamine), polyphosphazene and a polyethyleneoxide-polypropyleneoxide block copolymer, or the scaffold fibers are formed of one or more biodegradable components selected from the group consisting of polycaprolactone, polydioxanone, polyglycolic acid, poly(L-lactide) (PLLA), poly(DL-lactide-co-glycolide) (PLGA), polylactic acid and polyvinyl alcohol.

4. The yarn according to claim 1, wherein the slitting yarn has a width of 0.1 to 8 mm.

5. The yarn according to claim 1, wherein a physiologically active component promoting induction of one or more of adhesion, migration, growth, proliferation and differentiation of cells is fixed to the slitting yarn.

6. The yarn according to claim 5, wherein the physiologically active component includes one or more selected from the group consisting of a monoamine, an amino acid, a peptide, a saccharide, a lipid, a protein, a glucoprotein, a glucolipid, a proteoglycan, a mucopolysaccharide, a nucleic acid, and a cell.

7. A cell incubator, comprising:
the yarn for a cell culture scaffold according to claim 1; and
a cell cluster cultured in outer and inner spaces of the slitting yarn of the yarn.

8. The cell incubator according to claim 7, wherein the cell cluster includes any one or more types of stem cells selected from the group consisting of totipotent stem cells, pluripotent stem cells, multipotent stem cells, oligopotent stem cells and single stem cells, and/or one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

9. A fabric for cell culture, comprising the yarn for a cell culture scaffold according to claim 1.

* * * * *

```
SEQUENCE LISTING

<160> NUMBER OF SEQ ID NOS: 28

<210> SEQ ID NO 1
<211> LENGTH: 196
<212> TYPE: PRT
<213> ORGANISM: Artificial Sequence
<220> FEATURE:
<223> OTHER INFORMATION: Motif for cell culture scaffold

<400> SEQUENCE: 1

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Tyr Lys Tyr Lys Asn Ser Gly
                100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
    130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys
        195

<210> SEQ ID NO 2
<211> LENGTH: 202
<212> TYPE: PRT
<213> ORGANISM: Artificial Sequence
<220> FEATURE:
<223> OTHER INFORMATION: Motif for cell culture scaffold

<400> SEQUENCE: 2

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30
```

```
Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Ser Ser Glu
 50                  55                  60

Glu Tyr Lys Gly Gly Tyr Tyr Pro Gly Asn Thr Tyr His Tyr His Ser
 65                  70                  75                  80

Gly Gly Ser Tyr His Gly Ser Gly Tyr His Gly Gly Tyr Lys Gly Lys
                 85                  90                  95

Tyr Tyr Gly Lys Ala Lys Lys Tyr Tyr Lys Tyr Lys Asn Ser Gly
                100                 105                 110

Lys Tyr Lys Tyr Leu Lys Lys Ala Arg Lys Tyr His Arg Lys Gly Tyr
                115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys Gly Arg Gly Asp Ser Pro
            195                 200

<210> SEQ ID NO 3
<211> LENGTH: 172
<212> TYPE: PRT
<213> ORGANISM: Artificial Sequence
<220> FEATURE:
<223> OTHER INFORMATION: Motif for cell culture scaffold

<400> SEQUENCE: 3

Met Ala Lys Pro Ser Tyr Pro Pro Thr Tyr Lys Ala Lys Pro Ser Tyr
 1               5                  10                  15

Pro Pro Thr Tyr Lys Ala Lys Pro Ser Tyr Pro Pro Thr Tyr Lys Ala
                 20                  25                  30

Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Pro Trp Ala
 50                  55                  60

Asp Tyr Tyr Gly Pro Lys Tyr Gly Pro Pro Arg Arg Tyr Gly Gly
 65                  70                  75                  80

Asn Tyr Asn Arg Tyr Gly Arg Arg Tyr Gly Gly Tyr Lys Gly Trp Asn
                 85                  90                  95

Asn Gly Trp Lys Arg Gly Arg Trp Gly Arg Lys Tyr Tyr Gly Ser Ala
                100                 105                 110

Lys Pro Ser Tyr Pro Pro Thr Tyr Lys Ala Lys Pro Ser Tyr Pro Pro
            115                 120                 125

Thr Tyr Lys Ala Lys Pro Ser Tyr Pro Pro Thr Tyr Lys Ala Lys Pro
130                 135                 140

Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170

<210> SEQ ID NO 4
```

```
<211> LENGTH: 46
<212> TYPE: PRT
<213> ORGANISM: Artificial Sequence
<220> FEATURE:
<223> OTHER INFORMATION: Motif for cell culture scaffold

<400> SEQUENCE: 4

Ala Asp Tyr Tyr Gly Pro Lys Tyr Gly Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 5
<211> LENGTH: 76
<212> TYPE: PRT
<213> ORGANISM: Artificial Sequence
<220> FEATURE:
<223> OTHER INFORMATION: Motif for cell culture scaffold

<400> SEQUENCE: 5

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 6
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 6

Ala Lys Pro Ser Tyr Pro Pro Thr Tyr Lys
1               5                   10

<210> SEQ ID NO 7
<211> LENGTH: 60
<212> TYPE: PRT
<213> ORGANISM: Artificial Sequence
<220> FEATURE:
<223> OTHER INFORMATION: Motif for cell culture scaffold

<400> SEQUENCE: 7

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 8
```

```
<211> LENGTH: 3
<212> TYPE: PRT
<213> ORGANISM: Artificial Sequence
<220> FEATURE:
<223> OTHER INFORMATION: Motif for cell culture scaffold

<400> SEQUENCE: 8

Arg Gly Asp
1

<210> SEQ ID NO 9
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 9

Arg Gly Asp Ser
1

<210> SEQ ID NO 10
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 10

Arg Gly Asp Cys
1

<210> SEQ ID NO 11
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 11

Arg Gly Asp Val
1

<210> SEQ ID NO 12
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 12

Arg Gly Asp Ser Pro Ala Ser Ser Lys Pro
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 13

Gly Arg Gly Asp Ser
1               5

<210> SEQ ID NO 14
<211> LENGTH: 6
```

```
<212> TYPE: PRT
<213> ORGANISM: Artificial Sequence
<220> FEATURE:
<223> OTHER INFORMATION: Motif for cell culture scaffold

<400> SEQUENCE: 14

Gly Arg Gly Asp Thr Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Motif for cell culture scaffold

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Motif for cell culture scaffold

<400> SEQUENCE: 16

Gly Arg Gly Asp Ser Pro Cys
1               5

<210> SEQ ID NO 17
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 17

Tyr Arg Gly Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Motif for cell culture scaffold

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Motif for cell culture scaffold

<400> SEQUENCE: 19

Trp Gln Pro Pro Arg Ala Arg Ile
1               5

<210> SEQ ID NO 20
<211> LENGTH: 12
<212> TYPE: PRT
```

```
<213> ORGANISM: Artificial Sequence
<220> FEATURE:
<223> OTHER INFORMATION: Motif for cell culture scaffold

<400> SEQUENCE: 20

Asn Arg Trp His Ser Ile Tyr Ile Thr Arg Phe Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 22

Lys Ala Phe Asp Ile Thr Tyr Val Arg Leu Lys Phe
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 23

Ile Lys Val Ala Asn
1               5

<210> SEQ ID NO 24
<211> LENGTH: 16
<212> TYPE: PRT
<213> ORGANISM: Artificial Sequence
<220> FEATURE:
<223> OTHER INFORMATION: Motif for cell culture scaffold

<400> SEQUENCE: 24

Lys Lys Gln Arg Phe Arg His Arg Asn Arg Lys Gly Tyr Arg Ser Gln
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: Motif for cell culture scaffold

<400> SEQUENCE: 25

Val Ala Glu Ile Asp Gly Ile Gly Leu
1               5

<210> SEQ ID NO 26
<211> LENGTH: 10
<212> TYPE: PRT
<213> ORGANISM: Artificial Sequence
```

```
<220> FEATURE:
<223> OTHER INFORMATION: Motif for cell culture scaffold

<400> SEQUENCE: 26

Pro His Ser Arg Asn Arg Gly Asp Ser Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 27

Asn Arg Trp His Ser Ile Tyr Ile Thr Arg Phe Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 28

Thr Trp Tyr Lys Ile Ala Phe Gln Arg Asn Arg Lys
1               5                   10
```